(12) United States Patent
Momol et al.

(10) Patent No.: US 7,018,641 B1
(45) Date of Patent: Mar. 28, 2006

(54) MATERIALS AND METHODS FOR THE CONTROL OF PLANT PATHOGENS

(75) Inventors: Timur Mehmet Momol, Tallahassee, FL (US); David James Mitchell, Hawthorne, FL (US); Steve M. Olson, Quincy, FL (US); Esengul A. Momol, Tallahassee, FL (US)

(73) Assignee: University of Florida, Gainesville, FL (US)

( * ) Notice: Subject to any disclaimer, the term of this patent is extended or adjusted under 35 U.S.C. 154(b) by 0 days.

(21) Appl. No.: 09/925,336

(22) Filed: Aug. 9, 2001

Related U.S. Application Data

(60) Provisional application No. 60/223,903, filed on Aug. 9, 2000, provisional application No. 60/288,469, filed on May 31, 2001.

(51) Int. Cl.
*A61K 35/78* (2006.01)

(52) U.S. Cl. ...................................... 424/405; 424/725

(58) Field of Classification Search ................ 424/405, 424/725
See application file for complete search history.

(56) References Cited

U.S. PATENT DOCUMENTS 4,259,317 A    3/1981  Vesely et al.
4,574,083 A    3/1986  Baker et al.
4,780,471 A  * 10/1988  Maeda et al.
4,868,203 A  *  9/1989  Ueno et al.

FOREIGN PATENT DOCUMENTS

CA    2012288 A1 *  9/1990

OTHER PUBLICATIONS

Momol et al. Phytopathology (Jun. 2000), vol. 90, No. 6, pp. S127.*
Momol et al. Phytopathology (Jun. 1999), vol. 89, No. 6, pp. S54.*
Soler-Serratosa (Nematropica (1996), vol. 26, No. 1, pp. 57-71).*
Vesely, D., "Potential Biological Control of Damping-off Pathogens in Emerging Sugar Beet by *Pythium oligandrum* Drechsler" *Phytopath. Z*, vol. 90, pp 113-115, 1977, Paul Parey, Berlin und Hamburg.
Deacon, J.W., "Studies On *Pythium Oligandrum*, An Aggressive Parasite Of Other Fungi" *Trans. Br. mycol. Soc.*, vol. 66, No. 3, pp. 383-391, 1976, Printed in Great Britain.

* cited by examiner

*Primary Examiner*—Susan D. Coe
(74) *Attorney, Agent, or Firm*—Saliwanchik, Lloyd & Saliwanchik

(57) ABSTRACT

The subject invention provides compositions useful for the control of plant pathogens. Specifically exemplified are essential oil compositions which are effective in the control of fungal and bacterial plant pathogens.

1 Claim, 1 Drawing Sheet

MATERIALS AND METHODS FOR THE CONTROL OF PLANT PATHOGENS

CROSS-REFERENCE TO RELATED APPLICATION

This application claims priority from provisional patent applications U.S. Ser. No. 60/288,469, filed May 31, 2001 and U.S. Ser. No. 60/223,903, filed Aug. 9, 2000.

BACKGROUND OF THE INVENTION

Plants are subject to attack by a great number of pathogens. These pathogens can be, for example, bacteria, fungi, or nematodes. Pesticidal compounds have long been used to increase yields and extend agricultural production capabilities into new areas. They have also been extremely important tools for ameliorating season-to-season differences in yield and quality caused by weather-driven variations in disease pressure.

The future role of pesticides in agriculture is increasingly threatened by several factors including; the development of pest resistance, increasing concerns about food safety, and environmental accumulation of toxic compounds. As older pesticides are removed from the market due to regulatory changes, and new pesticides are becoming increasingly expensive to register, there is an increasing need to find ways to more wisely use the remaining, safest pesticides. This is particularly true for the many crop/disease combinations which do not represent large enough markets to pay for the cost of new compound registration. Wiser pesticide use will include ways to reduce application rates (and thus potential residues), finding ways to extend registrations to new crops, and identifying new compositions and treatments to combat the development of pest resistance.

Chemical pesticides have provided an effective method of control; however, the public has become concerned about the amount of residual chemicals which might be found in food, ground water and the environment. Stringent new restrictions on the use of chemicals and the elimination of some effective pesticides from the market place could limit economical and effective options for controlling pests. In addition, the regular use of chemical toxins to control unwanted organisms can select for resistant strains.

Alternative strategies to pesticide application are needed for the control of agriculturally important pests. Such strategies will help address public concern regarding pesticide pollution, as well as the perception that pesticide residues on food pose a threat to human health.

Among the more destructive zoosporic plant pathogens are the downy mildews (which are primarily associated with severe foliar diseases of many crops), and numerous species in the genus *Pythium* and *Phytophthora* which are destructive pathogens of roots, foliage, and fruits. Within the fungal genus *Pythium* are plant pathogenic species which can cause significant losses in vegetable production.

The value of vegetable crops grown in the state of Florida totaled over $1.79 billion for the 1991–92 crop season with much of the cabbage, cucumber, pepper, and tomato crops planted as transplants. Tomato alone accounts for $735 million in this production total and over 80% of the crop is transplanted. The use of vegetable transplants in commercial field production systems is important in many areas of the United States. In California, all of the celery, fresh market tomato and pepper, and most of the cauliflower and broccoli are grown as transplant crops. In Monterey County alone, the value of the transplants grown in 1992 amounted to nearly $18 million and represented a final crop value of $176 million.

Plant pathogenic *Pythium* species can kill a plant at the seedling stage or can reduce crop yield by destroying the root system of a mature plant. While diseases in the seedling stage are often controlled by fungicide application, the continued use of certain highly effective fungicides, e.g., metalaxyl, has faced regulatory uncertainty for use in vegetable transplant greenhouse production systems. In addition, continued use of a particular fungicide can result in the development of tolerance by the pathogen. Fumigants such as methyl bromide, which are routinely used on high cash-value crops, also face regulatory uncertainty. Thus, disease control (in particular damping-off) in the production greenhouses as well as in the field following transplanting are a major concern.

An alternative to the use of chemical pesticides for controlling phytopathogenic *Pythium* spp. is the use of biological control agents for vegetable transplants, a large and expanding industry in which disease protection is needed in the greenhouse as well as in the field after transplanting.

U.S. Pat. No. 4,574,083 to Baker and Lifshitz describes *Pythium nunn*, which is not pathogenic to plants and can protect seedlings from damping-off in greenhouse evaluations.

There are a number of studies examining the effect of seed treatment with oospores of *P. oligandrum* on reducing subsequent levels of disease, most of which have been conducted in the greenhouse. Deacon (1976; Trans. Br. Mycol. Soc. 66:383–391) described the ability of mycelial seed coatings on wheat to significantly reduce the disease incidence over untreated seeds.

Vesely (1977; Phytopath Z. 90:113–115; 1979) observed that application of oospores to sugarbeet seed reduced damping-off incidence to a similar level as thiram treatment (see also Schippers, B. and W. Gams, eds. Academic Press, *Soil-Borne Plant Pathogens*). In U.S. Pat. No. 4,259,317, Vesely et al. describe the application of *Pythium* oligandrum, or "Polygandron."

Bacterial wilt caused by *Ralstonia solanacearum* (Rs) is a major disease problem in fresh tomato production fields in north Florida. Fusarium is also an important plant pathogen.

Damage to plants caused by nematodes is also a prevalent and serious economic problem. Nematodes cause widespread and serious damage in many plant species. Many genera of nematodes are known to cause such damage. Plant-parasitic nematodes include members of the Phylum Nematoda, Orders Tylenchida and Dorylaimide. In the Order Tylenchida, the plant-parasitic nematodes are found in two Super Families: Tylenchoidea and Criconematoidea. There are more than 100,000 described species of nematodes.

Currently, the most effective substance for soil treatment is methyl bromide. Methyl bromide is used in the control of pest insects, nematodes, weeds, pathogens, and rodents. In the United States, about 27,000 tons of methyl bromide is used annually in agriculture, primarily for soil fumigation, as well as for commodity and quarantine treatment, and structural fumigation. Globally, about 76,000 tons of methyl bromide are used each year.

When used as a soil treatment, methyl bromide is injected into the soil at a depth of 12 to 24 inches before a crop is planted. This will effectively sterilize the soil, killing the vast majority of soil organisms. Immediately after the methyl bromide is injected, the soil is covered with plastic tarps that hold most of the methyl bromide in the soil. The tarps are removed 24 to 72 hours later.

After the tarps are removed, much of the methyl bromide leaves the soil. The EPA estimates that about 50% to 95% of the methyl bromide in the soil eventually enters the atmosphere.

While methyl bromide in large doses can result in damage to the human nervous system and respiratory system, the greatest danger poised by methyl bromides is the damage to the ozone layer. According to the 1994 Assessment of Ozone Depletion, the Ozone Depletion Potential (ODP) of methyl bromide has been assessed to be 0.6. This makes the ODP of the methyl bromide fifty times more effective at destroying ozone than CFC's on a per molecule basis.

According to the Clean Air Act (1990 Amendments), all substances with an ODP of 0.2 or greater are to be phased out in the United States. This means that methyl bromide will need to be phased out. There has been legislation to ultimately prohibit the production and importation of methyl bromide in the United States. In addition, 160 countries have signed the Montreal Protocol, a treaty calling for the levels of ozone-depleting chemicals to be frozen at 1991 levels. Finally, the EPA is lobbying for nations to stop using methyl bromide all together.

In light of the environmental problems with methyl bromide, and the continuing need for a soil treatment, an environmentally safe chemical alternative has been sought. Thus, there remains a need for pathogen control methods which are more compatible with the need for affordable and effective disease control, a high degree of food safety, and minimal environmental impact.

BRIEF SUMMARY OF THE INVENTION

The subject invention provides essential oils that can be used for the control of plant pathogens. Advantageously, the subject invention provides fumigants that provide an alternative to methyl bromide and other pre-plant fumigants. According to the subject invention, in a preferred embodiment essential oils can be used to control bacterial and fungal soilborne diseases of vegetables, ornamental plants and other plants.

Specifically exemplified herein are essential oils from the following plants: Palmarosa (*Cymbopogon martini*), tea tree (*Melaleuca alternifolia*), lemongrass (*Cymbopogon flexuosus*) and *Eucalyptus citriodora*. Additionally, thymol which is a fraction of thyme (*Thymus vulgaris*) oil was found effective to control plant diseases.

In a specific embodiment of the subject invention, geraniol, which is a fraction of palmarosa, can be used to effectively control plant pathogens. Specifically, exemplified herein is the use of geraniol and/or palmarosa oil against the bacterial wilt pathogen.

The essential oils of the subject invention and their derivatives are highly advantageous for pesticidal use because they occur commonly in nature, have little mammalian toxicity, are compatible with other biological control strategies and are readily broken down to innocuous components.

FIG. 2 shows the effect of thymol on the colony development of *Ralstonia solanacearum.*

DETAILED DISCLOSURE OF THE INVENTION

The subject invention concerns unique materials and methods for the effective and environmentally safe control of plant pathogens. In each embodiment of the subject invention, plant essential oil compositions constitute a critical component of the control strategy. As described in detail below, the essential oil component may be a salt or derivative. As used herein, reference to "essential oil" should be understood to include salts and derivatives thereof.

A description of essential oils can be found at, for example, Guenther, Ernest, The essential oils (1972) Hungtington, N.Y., R.E. Krieger Pub. Co., which is incorporated herein by reference.

Essential oils of tea tree (*Melalcuca alternifolia*), marjoram (*Thymus masiichina*), oregano (*Origanum vulgure*), thyme (*Thymus vulgaris*) and palmarosa (*Cynbopogon martini*) were tested in vitro and in greehouse grown tomatoes for their efficacy against *Ralstonia solenacearum* (Rs). Also thymol, one of the fractions of thyme oil, was tested in vitro and in greenhouse. Thymol, the vapor effect of palmarosa and thyme essential oils are effective against Rs. Geraniol has also been found to be effective for the control of plant pathogens. In a preferred embodiment of the subject invention, essential oils can be integrated into the management of bacterial wilt and nematodes (such as *Meloides* sp.) on tomato.

Advantageously, the chemical compositions used according to the subject invention are environmentally safe. The active ingredients in the compositions are all plant extracts or are derived from plant extracts. In one embodiment, the compositions may comprise a surfactant that acts as a wetting agent. The wetting agent helps during the dilution of the chemical compositions in water. The wetting agent also helps the chemical composition saturate the soil. Preferably, a food grade surfactant can be used due to the use of the compositions as soil or plant treatments. An example of a suitable surfactant is polysorbate. The amount of surfactant can be readily determined by a person skilled in the art and should be sufficient to set fully the treated soil when the first dosage of composition is applied. This amount may change with soil composition and crop type. The balance of the composition can be completed with oil and water, and other compounds as appropriate.

The compositions and methods described herein can be used to control a broad range of fungal and bacterial targets. These targets include, but are not limited to species of *Penicillium* (i.e., *expansum, digitatum, italicum*), *Ralstonia* sp., *Botrytis* sp., *Monilinia* sp., *Alternaria* sp., *Aspergillus* sp., *Rhizopus* sp., members of the Erisyphales (powdery mildews *Sphaerotheca* sp., *Erisyphe* sp., *Uncinula* sp., *Podosphaera* sp.), members of the Peronosporales (downy mildews, *Phytopthora* sp., *Pythium* sp., *Peronospora* sp.) Hemibasidiomycetes (rusts and smuts), *Venturia* sp., *Cercospora* sp. *Pseudocercosporella* sp., *Cercospora* sp., *Cercosporidium* sp., *Fusarium* sp., *Ophiostoma* sp. and other wood staining fungi, and *Diplodia* sp., other targets include *Erwinia* sp., *Pseudomonas* sp., and *Xanthomonas* sp, and nematodes (including *Meloides* sp.).

These plant pests can be controlled on seeds, corms, bulbs, flowers, stems, leaves, exposed roots, and fruits of plants including, but not limited to, grapes, pears, apples, peaches, nectarines, grapefruit, cherries, apricots, lemons, oranges, mangos, bananas, and tangerines. The plants which may be treated further include, but are not limited to, potatoes, tomatoes, cucumbers, lettuce, rice, wheat, rye and other cereals, flower crops, and almonds.

Figure 1:
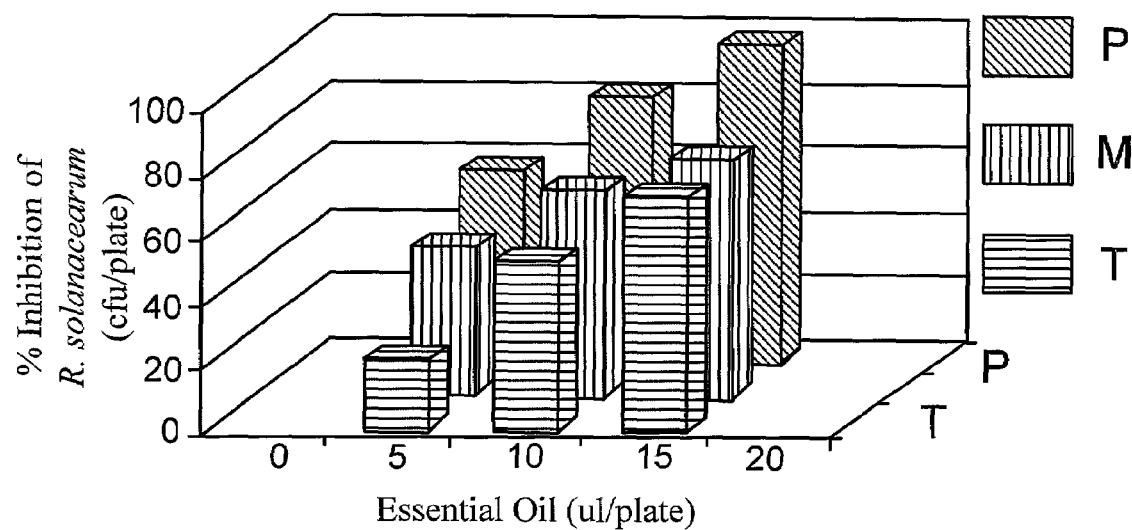
FIG. 1 shows the effect of selected essential oils on colony development of *Ralstonia solanacearum.*

As used herein, the term "produce" includes, but is not limited to, any of the plant surfaces listed above. Also, as used herein, the term "citrus" refers to fruits such as oranges, lemons, limes, grapefruit, and the like.

The compositions can also be applied to surfaces such as freshly cut lumber for the control of fungal or bacterial targets. The compositions of the subject invention can be used to control microbial plant disease on both dormant and non-dormant plant tissue. As known by those skilled in the art, non-dormant tissue includes growing vegetation and fruits (pre- and post-harvest).

In cases where essential oils are useful for eradication of existing infections of fruit, the further protection of that fruit from subsequent infections can be achieved by the simultaneous or subsequent application of a fungicide, bactericide, or a biological control organism in a dip or spray application. This application can also be made along with the application of various waxes or finishes which are commonly used with fruit. The formulation of such applications can also include nutrients which will benefit the establishment of the biocontrol organism.

Appropriate formulations and concentrations can be readily ascertained by those skilled in this art using the teachings of the subject invention.

The potent, activity of the compositions of the subject invention combined with other fungicides or bactericides makes it possible to achieve the same level of control while using a smaller quantity of the non-oil fungicide or bactericide component of the mixture. The compositions of the present invention can comprise a mixture of components wherein the mixture is sufficiently active so that application of the composition enables utilization of reduced amounts of each of the active ingredients while still providing effective activity. This is significant because lower use rates lead to lower residues on the crop or in the environment, lower costs of application, an expansion of the margin between crop safety and efficacy for fungicides which can be phytotoxic (thus enhancing their safety or expanding the crops, varieties or timings for their use), and lower total "market basket" exposure for a multi-use fungicide or bactericide.

Combinations of other fungicides or bactericides with essential oils offer additional advantages because of the particular mode of action of these materials. One such advantage is a reduction in selection pressure for resistant forms.

Chemical control agents which can be combined with essential oils according to the subject invention include, but are not limited to, benomyl, borax, captafol, captan, chlorothalonil, various formulations containing copper; various formulations containing zinc; dichlone, dicloran, iodine, various ergosterol biosynthesis inhibiting fungicides including but not limited to fenarimol, imazalil, myclobutanil, propiconazole, prochloraz, terbutrazole, flusilazole, triadimefon, and tebuconazole; folpet, iprodione, mancozeb, maneb, metalaxyl, oxycarboxin, oxytetracycline, PCNB, pentachlorophenol, quinomethionate, sodium arsenite, sodium DNOC, sodium hypochlorite, sodium phenylphenate, streptomycin, sulfur, thiabendazole, thiophanate-methyl, triforine, vinclozolin, zineb, ziram, tricyclazole, cymoxanil, blasticidin, and validimycin. The essential oils can also be combined with various spray oils.

Biological control agents that can be used according to the subject invention include but are not limited to *Bacillus* sp., *Pseudomonas* sp., *Trichoderma* sp., *Erwinia* sp., *Pichia* sp., *Candida* sp., *Cryptococcus* sp., *Talaromyces* sp., *P. fumosoreus*, *B. bassiana*, *Chaetomium* sp., *Gliocladium* sp., *Aureobasidium* sp., *Dabaryomyces* sp., *Exophilia* sp., *Ampelomyces* sp., and *Mariannaea* sp.

The invention also encompasses several methods for the treatment of soil. In one embodiment, the method involves diluting a concentrated solution in water. The diluted solution is then sprayed into the ground to a depth of 12 to 24 inches. The amount sprayed is the quantity necessary to saturate the soil. This amount is between typically about 1%–20% by weight of the soil being treated. The amount depends on the type of soil being treated and the crop being grown.

Among the further applications of the subject invention are the following:

the use of an essential oil to improve or compliment the activity of other fungicidal and bactericidal chemicals;

the use of an essential oil to provide control and to also perturb the plant surface microflora to enhance the subsequent colonization of that surface by a compatible biological control agent;

Following are examples which illustrate procedures for practicing the invention. These examples should not be construed as limiting. All percentages are by weight and all solvent mixture proportions are by volume unless otherwise noted.

Example-1

Figure 2:
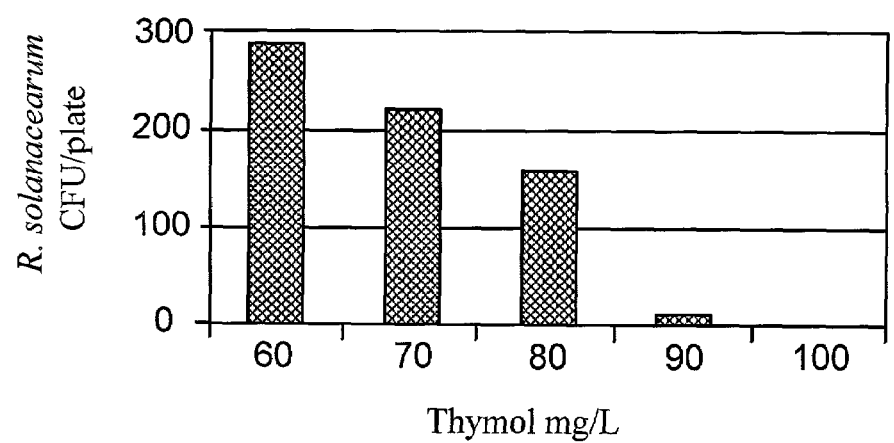

The essential oils tested showed volatile bactericidal activities in vitro against Ralstonia solanacearum. Essential oil from palmarosa showed the greatest inhibition of colony development (FIG. 1). Thymol at 100 µg/ml concentration entirely inhibited the development of *R. solanacearum* colonies (FIG. 2). In greenhouse tests, essential oils from thyme, palmarosa and wild marjoram resulted in significantly less disease than the inoculated untreated control (Table 1).

TABLE 1

Effect of essential plant oils and medicinal plants on bacterial wilt of tomato in greenhouse experiments.

| Treatments | Experiment 1 % Severity$^x$ | Experiment 2 % Severity$^x$ |
|---|---|---|
| Untreated Control | 80A | 100A |
| Wild Marjoram EO$^z$ | 0B | —$^y$ |
| Thyme EO | 0B | — |
| Palmarosa EO | 0B | 20B |
| Non-inoculated | 0B | 0B |

$^z$EO, essential oil; fresh, fresh plant material from leaves
$^y$—, not tested
$^x$Treatments followed by the same letter did not differ significantly at P = 0.01 level as determined by LSD range test.

Example-2

The efficacy of several essential oils were evaluated for management of the following soilborne fungi pathogens: *Fusarium oxysporum* f. sp. *lycopersici*, *Phytophthora capsici*, *Pythium aphanidermatum*, and *Athelia rolfsii*. In greenhouse tests using microwaved soil infested with fungal pathogens, infection of tomato roots and subsequent root rot caused by the four fungi was reduced or eliminated in soil treated before planting with palmarosa oil and, for *P. capsici* and *A. rolfsii*, by oils of wild marjoram and thyme (Table 2). Root weights generally were greater in soil infested with the four fungi and treated with palmarosa oil than in the infested, nontreated soil (Table 2). In conclusion, essential oils can be used as bio-fumigants for integrated management programs against soilborne pathogens of tomato and other host plants.

TABLE 2

Fresh weights of shoots and root systems, percentages of infection of 'Bonnie Best Improved' tomato roots, and plant mortality after inoculation[V]

| Pathogen | Essential Oil | Infection (%) | Mortality (%) | Root Disease[W] Rating | Surviving Plants at Harvest[X] | | |
|---|---|---|---|---|---|---|---|
| | | | | | No. | Shoot Weight (g) | Root Weight (g) |
| Uninfested wheat seed | Water | 100[Y] | 0 | 1.0a[Z] | 6 | 16.827a | 6.177a |
| Uninfested wheat seed | Wild Marjoram | 100 | 0 | 1.0a | 6 | 16.180ab | 5.041ab |
| Uninfested wheat seed | Palmarosa | 83 | 0 | 1.0a | 6 | 13.086abcd | 4.617abc |
| Uninfested wheat seed | Red Thyme | 100 | 0 | 1.0a | 6 | 14.741abc | 5.932a |
| *Fusarium oxysporum* f. sp. *lycopersici* | Water | 100 | 67 | 2.5cde | 2 | 2.078i | 0.238f |
| *Fusarium oxysporum* f. sp. *lycopersici* | Wild Marjoram | 100 | 67 | 2.0bc | 2 | 4.376hi | 0.288f |
| *Fusarium oxysporum* f. sp. *lycopersici* | Palmarosa | 100 | 0 | 1.0a | 6 | 11.526bcde | 4.603abc |
| *Fusarium oxysporum* f. sp. *lycopersici* | Red Thyme | 33 | 50 | 1.7b | 3 | 12.759fg | 2.344e |
| *Phytophthora capsici* | Water | 100 | 0 | 2.8de | 6 | 11.685bcde | 3.267cde |
| *Phytophthora capsici* | Wild Marjoram | 0 | 0 | 1.0a | 6 | 16.856a | f.f92ab |
| *Phytophthora capsici* | Palmarosa | 0 | 0 | 1.0a | 6 | 11.301cde | 4.504abc |
| *Phytophthora capsici* | Red Thyme | 0 | 0 | 1.0a | 6 | 15.677abc | 5.587ab |
| *Pythium aphanidermatum* | Water | 100 | 0 | 3.3e | 6 | 8.193ef | 2.826de |
| *Pythium aphanidermatum* | Wild Marjoram | 100 | 0 | 2.5cde | 6 | 12.387abcd | 4.129bcd |
| *Pythium aphanidermatum* | Palmarosa | 0 | 0 | 1.0a | 6 | 12.604abcd | 5.592ab |
| *Pythium aphanidermatum* | Red Thyme | 100 | 0 | 2.2bcde | 6 | 14.477abc | 5.024ab |
| *Athelia rolfsii* | Water | 83 | 33 | 2.0bc | 4 | 8.437fgh | 1.999e |
| *Athelia rolfsii* | Wild Marjoram | 0 | 0 | 1.0a | 6 | 14.819abc | 5.589ab |
| *Athelia rolfsii* | Palmarosa | 0 | 0 | 1.0a | 6 | 9.206def | 4.082bcd |
| *Athelia rolfsii* | Red Thyme | 0 | 17 | 2.0bc | 5 | 4.312ghi | 2.351e |

[V]Three-week-old tomato seedlings were grown in Boynton Beach soil which had been infested with the pathogen and the oil on 4-16-99 in closed bags, moved to the greenhouse and placed in pots in 4-19-99, and planted on 4-21-99.
[W]Root disease based on an index with 0 = no root symptoms; 1 = less than 25% of root tips necrotic; 2 = 25–50% of root tips necrotic; 3 = 50–100% of root tips necrotic plus localized necrotic lesions on the tap root or crown; 4 = extensive root rot with few or no white roots, crown rot extensive; 5 = root system completely necrotic and plant dead or moribund.
[X]Average fresh weights of shoots and roots of plants in each treatment at final havest on 5-19-99 and 5-20-99.
[Y]Fusarium olysporum recovered from control plants.
[Z]Values followed by the same letters in a column are not different according to Duncan's Multiple Range Test ($P \leq 0.05$).

Example 3

Use of Geraniol to Control Plant Pathogens

In accordance with the subject invention, geraniol has been shown to have volatile bactericidal activity against *Ralstonia solanacearum*. Geraniol reduced population of *Ralstonia solanacearum* signicantly (89.5%) compared to untreated control. Its effect was compared with palmarosa oil. In the same experiment, palmarosa oil reduced the population of Ralstonia solanacearum by 87.5%. Thus, geraniol was found to be highly effective against the bacterial wilt pathogen.

The efficacy of geraniol was also evaluated for management of the following soilborne fungi pathogens: *Fusarium oxysporum* f. sp. lycopersici, *Phytophthora capsici, Pythium aphanidermatum*, and *Athelia rolfsii*. In greenhouse tests using microwaved soil infested with fungal pathogens, infection of tomato roots and subsequent root rot caused by the four fungi was reduced or eliminated in soil treated before planting with geraniol. It was found that the effect of the geraniol is better, or equal to, the effect that is obtained with thymol. Thus, geraniol can be used effectively as a bio-fumigant for integrated management programs against soilborne pathogens of tomato and other host plants (including vegetables and ornamentals).

Example 4

General Formulations

A. Wettable powders. Wettable powders are water-dispersable compositions containing the active material, an inert solid extender, and one or more surfactants to provide rapid wetting.

The inert extenders which are preferred for use in the wettable powders of this invention containing the active compounds are of mineral or organic origin.

Extenders suitable for the wettable powder formulations of this invention are the natural clays, vermiculite, diatomaceous earth, and synthetic mineral fillers derived from silica and silicate. Most preferred filters for this invention are kaolinites, attapulgite clay, montmorillonite clays, synthetic silicas, synthetic magnesium silicate, and calcium sulfate dihydrate. A surface active agent can also be added to give a homogenous and stable formulation.

Among the more preferred surfactants are the nonionic and anionic types. They are most suitable for the preparation of dry, wettable products of this invention and dispersants. Occasionally a liquid, non-ionic compound which is primarily an emulsifier may serve as both wetter and dispersant.

Most preferred wetting agents are alkylbenzene and alkylnaphthalene sulfonates, sulfated fatty alcohols, amines, or acid amides, long chain esters of sodium isethionate, esters of sodium sulfosuccinate, sulfated or sulfonated vegetable oils, and ditertiary acetylenic glycols. Preferred dispersants are methyl cellulose, polyvinyl alcohol, lignin sulfonates, polymeric alkylnaphthalene sulfonates, sodium naphthalene sulfonates, polymethylene bisnaphthalene sulfonate, and sodium-N-methyl-N-(long chain acid) taruates.

Wetting and dispersing agents in these preferred wettable powder compositions of the invention are usually present at concentrations of from about 0.5 weight percent to 5 weight percent. The inert extender then completes the formulation. Where needed, 0.1 weight percent of the extender may be replaced by a corrosion inhibitor or an anti-foaming agent or both.

Thus, wettable powder contains a corrosion inhibitor or an anti-foaming agent or both, the corrosion inhibitor should not exceed about 1 percent of the composition, and the anti-foaming agent should not exceed about 0.5 percent by weight of the composition, both replacing equivalent amounts of the inert extender.

B. Dusts. Dusts are dense powder compositions which are intended for application in dry form. Dusts are characterized by their free-flowing and rapid settling properties so that they are not readily windborne to areas where their presence is not desired. They contain primarily an active ingredient and a dense, free-flowing, solid extender. Their performance is sometimes aided by the inclusion of a wetting agent and convenience in manufacture frequently demands the inclusion of an inert absorptive grinding aid.

The wettable powder as described above can also be used in the preparation of dusts. While such wettable powders can be used directly in dust form, it is more advantageous to dilute them by blending with the dense dust diluent. In this manner, dispersing agents, corrosion inhibitors, and antifoam agents may also be used as components of a dust.

Thus, the dust compositions of this invention can comprise from about 0.5 to 20.0 weight percent active ingredient, 5 to 25 weight percent filler, 0.0 to 1.0 weight percent wetting agent, and from about 30 to 90 weight percent dense, free-flowing extender, as these terms are used herein. Such dust formulations can contain, in addition, minor amounts of dispersants, corrosion inhibitors, and anti-foam agents derived from the wettable powders used to make the dust.

C. Emulsifiable oils. Emulsifiable oils are usually solutions or suspensions of active material in non-water miscible solvents together with a surfactant and/or emulsifier.

For compositions of this invention, emulsifiable oil compositions can be made by mixing the active ingredient with an organic solvent and surfactant. Suitable solvents for the compositions of this invention are chlorinated solvents, water immiscible ethers, esters, or ketones alone or in admixture with aromatic hydrocarbons. Suitable surfactants are those ionic or non-ionic agents known to the art as emulsifying agents.

Emulsifying agents most suitable for the emulsifiable oil compositions of this invention are long chain alkyl or mercaptan polyethoxy alcohols, alkylaryl polyethoxy alcohols, sorbitan fatty acid esters, polyoxyethylene ethers with sorbitan fatty acid esters, polyethylene glycol esters with fatty rosin acids, fatty alkylol amide condensates, calcium and amine salts of fatty alcohol sulfates, oil soluble petroleum sulfonates, or preferably mixtures of these emulsifying agents should comprise from about 1 to 10 weight percent of the total composition. As described above, however, up to 5 parts of emulsifying agent for each part of active ingredient can be used.

Thus, emulsifiable oil compositions of the present invention can consist of from about 10 to 50 weight percent active ingredient, about 40 to 82 percent solvents, and about 1 to 10 weight percent emulsifier, as these terms are defined and used above.

D. Granules. Granules are physically stable, particulate compositions containing spores and/or mycelia of this invention which adhere to or are distributed through a basic matrix of a coherent, inert carrier with microscopic dimensions. In order to aid leaching of the active ingredient from the granule, a surfactant can be present.

The inert carrier is preferably of mineral origin, and suitable carriers are natural clays, some pyrophyllites and vermiculite. Suitable wetting agents can be anionic or nonionic.

For the granule compositions of this invention, most suitable carriers are to two types. The first are porous, absorptive pre-formed granules, such as preformed and screened granular attapulgite or heat expanded, granular, screened vermiculite. On either of these, a solution of the active agent can be sprayed and will be absorbed at concentrations up to 25 weight percent of the total weight. The second type are initially powdered kaolin clays, hydrated attapulgite, or bentonite clays in the form of sodium calcium, or magnesium bentonites. Water-soluble salts such as sodium salts may also be present to aid in the disintegrations of the granules in the presence of moisture. These ingredients are blended with the active component distributed uniformly throughout the mass. Such granules can also be made with 25 to 30 weight percent active component but more frequently a concentration of about 10 weight percent is desired for optimum distribution. The granular compositions of this invention are believed to be most useful in a size range of 15–30 mesh.

The most suitable wetting agents for the granular compositions of this invention depend upon the type of granule used. When pre-formed granules are sprayed with active material in liquid form, the most suitable wetting agents are non-ionic, liquid wetters miscible with the solvent. These are more generally known in the art as emulsifiers and comprise alkylaryl polyether alcohols, alkyl polyether alcohols, polyoxethylene sorbitan fatty acid esters, polyethylene glycol esters with fatty or rosin acids, fatty alkylol amide condensates, oil petroleum or vegetable oil sulfonates, or mixtures of these. Such agents will usually comprise up to about 5 weight percent of the total composition.

When the active ingredient is first mixed with a powdered carrier and subsequently granulated, liquid non-ionic wetters can still be used, but it is usually preferable to incorporate at the mixing stage one of the solid, powdered anionic wetting agents such as those previously listed for the wettable powders. Such agents should comprise about 0 to 2 percent of the total composition.

Thus, the preferred granular formulation of this invention comprises about 5 to 30 weight percent active material, about 0 to 5 weight percent wetting agent, and about 65 to 95 percent inert mineral carrier, as these terms are used herein.

A further aspect of the subject invention pertains to containers in which the compositions of the subject invention are sold and/or distributed. In a preferred embodiment, these containers contain the plant essential oil formulations and have instructions for the use of the essential oils for the control of plant pathogens. In a preferred embodiment, the containers are plastic (or other appropriate inert material). The formulation is preferably concentrated but may also be diluted for immediate use. In a preferred embodiment, the instructions pertain to the use of the plant essential oils as fumigants for the control of plant pests. In a further preferred embodiment, the instructions for use are written on the outside of the container.

Example 5

Specific Formulations

Specific formulations which can be used according to the subject invention as bio-fumigants for field application include the following:

UFBF771: 8 ml Pure *Cymbopogon Martini* Oil, 2 ml 95% Ethyl alcohol, 1 ml detergent, 9 ml water (total volume of 20 ml).

UFBF772: 8 ml Pure *Melaleuca* Altemifolia Oil, 2 ml 95% Ethyl alcohol, 1 ml detergent, 9 ml water (total volume of 20 ml).

UFBF773: 8 ml Pure *Cymbopogon Flexuosus* Oil, 2 ml 95% Ethyl alcohol, 1 ml detergent, 9 ml water (total volume of 20 ml).

UFBF774: 8 ml Pure *Eucalyptus Citriodora* Oil, 2 ml 95% Ethyl alcohol, 1 ml detergent, 9 ml water (total volume of 20 ml).

A person skilled in the art, having the benefit of the instant disclosure could readily prepare various volumes of the pesticidal composition described herein.

Pure essential oils can be readily purchased. Based on these formulations (mixture of essential oils with other ingredients as needed), a stable emulsion can be readily prepared and applied with an injector.

These compositions are effective against soil-borne fungi such as *Fusarium, Pythium, Phytophthora* and *Sclerotium rolfsil* and bacterial wilt (Ralstonia solanacearum). Nematodes can also be treated.

Example 6

Specific Protocol for Field Use

In a specific embodiment, the bio-fumigants can be applied using single injector to a 30 cm depth. A total volume of 20 ml can be applied to every 30 cm of the soil covered with plastic mulch.

The following procedure can be used for field application including small plot field experiments:
1) Cover the beds with plastic mulch.
2) Open small holes every 15 inch. With an injector, liquid formulation can be injected.
3) The openings can be sealed immediately for at least 15 days.
4) Open the holes for transplants, wait 10 days before transplanting.

A total of 25 days can be left between application and planting.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A method for reducing damage to tomato plants caused by *Ralstonia solanacearum* wherein said method consists essentially of applying to soil, as a fumigant, a composition consisting essentially of thymol, ethanol and a detergent, wherein the concentration of ethanol is at least 1%, wherein tomato plants are planted in the soil within 25 days of the application of the fumigant to the soil, and wherein the use of said fumigant results in an increase in the market basket of tomatoes due to the control of *Ralstonia solanacearum* without phytotoxicity to the tomato plants.

* * * * *